United States Patent [19]
Lane et al.

[11] Patent Number: 4,990,333
[45] Date of Patent: Feb. 5, 1991

[54] METHOD FOR HEALING BONE DAMAGE

[75] Inventors: Joseph Lane, New York, N.Y.; Nicholas Catsimpoolas, Newton Centre, Mass.; Robert S. Sinn, New York, N.Y.

[73] Assignees: Angio Medical Corporation, New York, N.Y.; Trustees of Boston University, Boston, Mass.

[21] Appl. No.: 811,894

[22] Filed: Dec. 20, 1985

[51] Int. Cl.$^5$ .............................................. A01N 63/02
[52] U.S. Cl. .................................. 424/551; 424/572; 514/54; 514/25; 800/2; 800/DIG. 5
[58] Field of Search ...................... 514/54; 424/95, 104

[56] References Cited

U.S. PATENT DOCUMENTS

| | | | |
|---|---|---|---|
| 3,318,774 | 5/1967 | Dingwall et al. | 424/95 |
| 4,108,849 | 8/1978 | Thomas | 424/104 |
| 4,301,064 | 11/1981 | Bohn | 424/104 |
| 4,347,244 | 8/1982 | Mynard et al. | 424/180 |
| 4,388,309 | 6/1983 | Fabricius et al. | 424/180 |
| 4,394,370 | 7/1983 | Jefferies | 424/95 |
| 4,456,596 | 6/1984 | Schäfer . | |
| 4,544,552 | 10/1985 | Fraefel et al. . | |
| 4,637,931 | 1/1987 | Schmitz | 424/95 |
| 4,642,120 | 2/1987 | Nevo et al. | 424/95 |

FOREIGN PATENT DOCUMENTS

| | | |
|---|---|---|
| 0038511 | 10/1981 | Fed. Rep. of Germany . |
| 0095682 | 12/1983 | Fed. Rep. of Germany . |
| 799241 | 8/1958 | United Kingdom ................ 424/95 |
| 898105 | 6/1962 | United Kingdom ................ 424/95 |

OTHER PUBLICATIONS

Rabinowtiz, J. I., et al. (1978), "Lipid Composition and Biosynthesis of Human Omental Tissue", vol. 13, No. 5, pp. 317–322.

Biological Abstracts/Reports, Reviews and Meetings, vol. 28, 1985, (Philadelphia, US), H. S. Goldsmith et al.: "Lipid Angiogenic Factor From Amentum", see abstract No. 28135, & J.A.M.A. (Journal of the American Medical Association), 1984, vol. 252, No. 15, pp. 2034–2036 cited in the application.

Chemical Abstracts, vol. 89, No. 13, Sep. 25, 1978, (Columbus, OH, US), J. I. Rabinowitz et al.: "Lipid Composition and Biosynthesis of Human Mental Tissue", see page 523, Abstract 104765g, & Lipids, 178, 13(5), 317–322.

Komoda, et al., "Multiple Forms . . . , Igaka no Ayumi", 136 (10) 765–6, 1986.

Train, J. Lipid Res. 22 (8) 1271–6, "Cakcholamines".

Morris, Selenium Biol Med. (Proc. Int. Syrup) 2nd, Meeting Date 1BbK, 438–48, 1981.

"Distribution of DDT", Vrach. Delo, (1) 129–32, 1974.

Watanube, "Ultrastructural . . . ", Recent Advan. RES, Res. 11, 120–47, 1973.

Merck Handbook, 10th Ed. "Gangliosides", p. 623.

Condensed Chemical Dictionary 9th Ed., "Lipid", p. 515.

Primary Examiner—Mary C. Lee
Assistant Examiner—Catherine S. Kilby Scalzo
Attorney, Agent, or Firm—Felfe & Lynch

[57] ABSTRACT

Factors isolated from omental extracts are used to promote bone healing, for example in fractures in mammals.

1 Claim, 2 Drawing Sheets

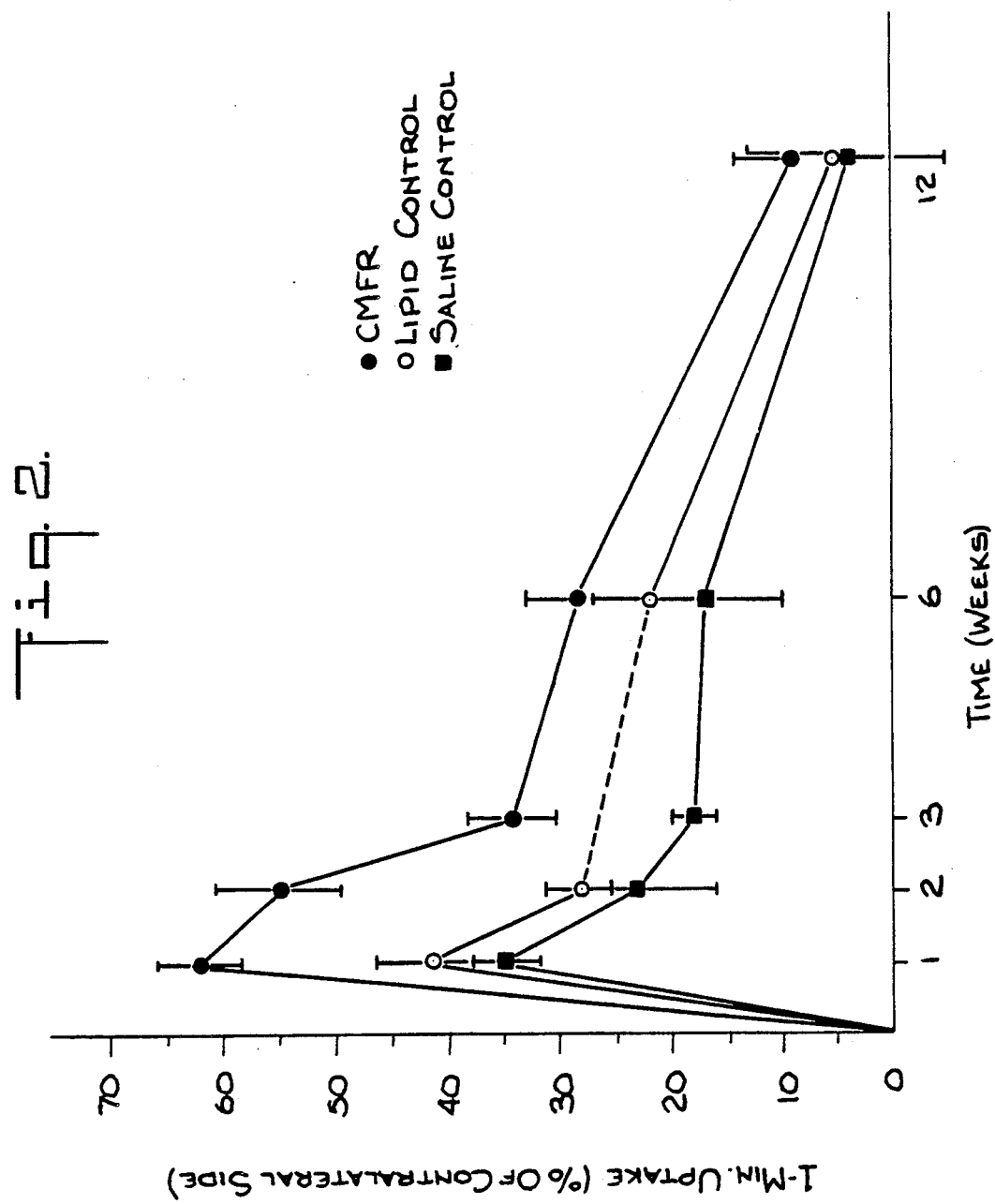

METHOD FOR HEALING BONE DAMAGE

This invention concerns healing of bone damage using angiogenic compositions from mammalian omenta.

SUMMARY

Omental lipid compositions are used to promote healing of bone fractures in mammals.

DESCRIPTION OF THE DRAWING

FIG. 2 measures bone uptake of radioisotope with time (weeks) measuring perfusion to the bone.

DESCRIPTION

Figure 1:
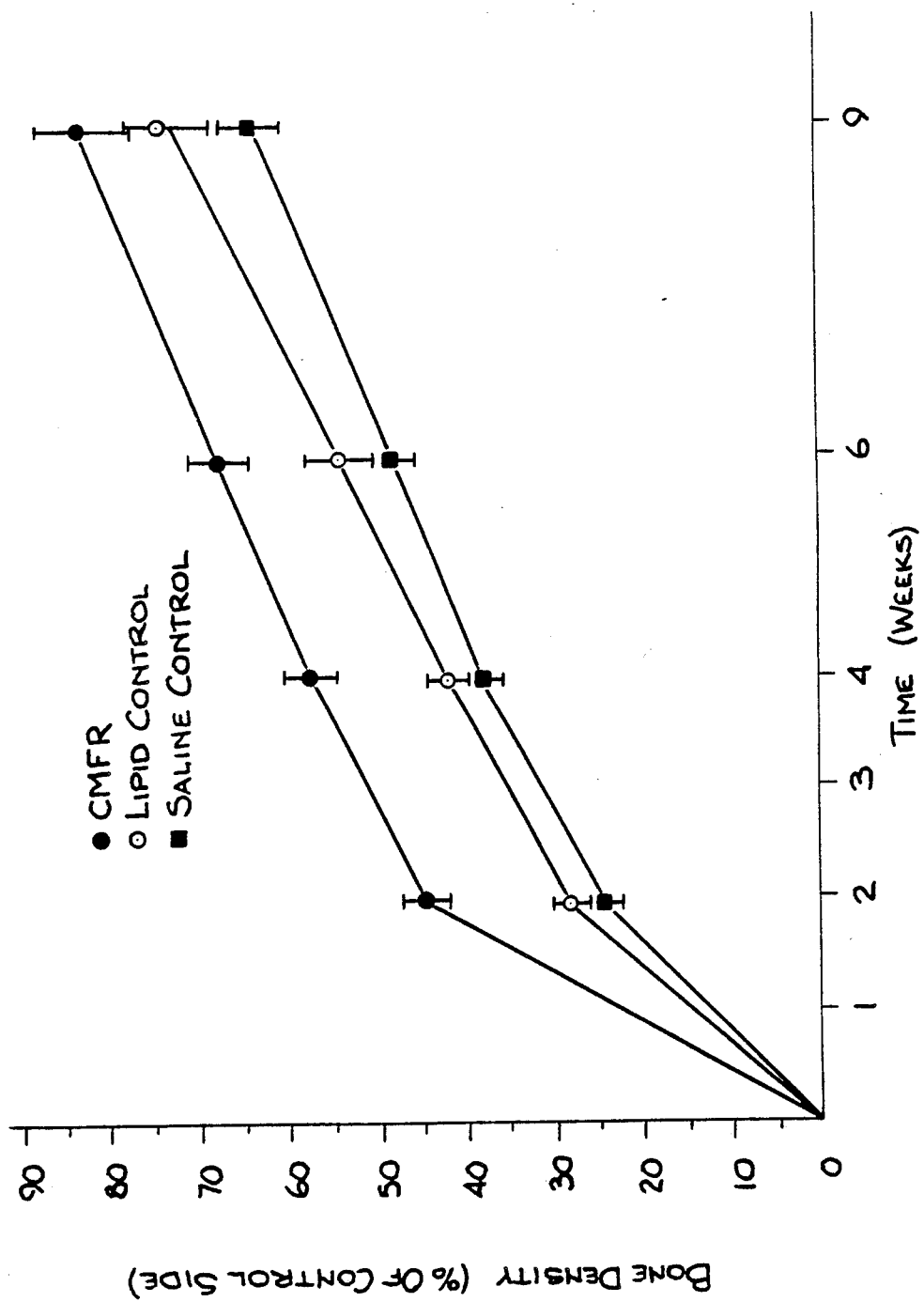
FIG. 1 shows the increase in bone density with time in weeks for groups A, B and C.

Bone healing is generally hampered by the fact that bone material does not have a good blood supply and in the case of a bone fracture there is loss of blood supply to the area with the bone fracture as well as necrotic area around the bone fracture.

The art treats such conditions with mechanical support—casts, pins and traction. Metal and plastic prosthetic devices such as artificial joints and bone grafts are used as well for bone replacement therapy. The art also involves use of various materials or frameworks which serves as a support for bone growth.

We also see in the art use of synthetic materials such as polyurethane and other isocryanate materials in orthopedic surgery as in U.S. Pat. No. 3,030,951 to Mandarino issued Apr. 24, 1962. Ashman et al use acrylic prosthesis which include barium Sulfate in U.S. Pat. No. 4,535,485 issued Aug. 20, 1985 and U.S. Pat. No. 4,547,390 issued Oct. 15, 1985 and U.S. Pat. No. 4,547,390 issued Oct. 15, 1985. This acrylic technique appears to be applicable mainly to tooth replacement as in U.S. Pat. No. 4,547,327 to Bruins et al. issued Oct. 15, 1985 and U.S. Pat. No. 4,536,158 issued Aug. 20, 1985.

Mattei et al (U.S. Pat. No. 4,440,789 issued Apr. 3, 1984) employ polydioxane but here the object is to control bleeding from cut bone surfaces and the material used is absorbed by the body. Mattei et al use a fatty acid salt also in a base for the above purpose as well in U.S. Pat. No. 4,439,420 issued Mar. 27, 1984.

Other natural materials transformed for bone filling or replacement purposes include regenerated, demineralized bone and tooth material (U.S. Pat. No. 4,172,128 issued Oct. 23, 1979 to Theile et al), fibrinogen (U.S. Pat. 4,442,655 issued Apr. 17, 1984 to Stroltmann), collagen for bone or soft tissue (U.S. Pat. No. 3,949,073 issued Apr. 6, 1976 to Daniels et al), calcium crystals from coral serve as a matrix or support for bone growth, autografts are used by Sully et al. (U.S. Pat. No. 4,385,404 issued May 31, 1983) and bioprosthesis have some use in soft tissue as well (See U.S. Pat. No. 4,400,833 issued Aug. 30, 1983 to Kerland).

There is nothing in the art dealing with a biologically active biochemical composition to promote bone healing. Fabricius et al. in U.S. Pat. No. 4,388,309 issued June 4, 1983 use a desialylated ganglioside agent to suppress transplantation rejection phenomena but this relates only to a bone marrow transplant with no object as to bone healing. Charley, M. R. et al report (J. Immunol. November 1983, 131:2101) however use of anti-asialo GM, on a murine model in Graft v. host disease (GVHD).

Inhibition of bone resorption is seen in U.S. Pat. No. 4,176,177 issued Nov. 27, 1979 to Kuettner but this material is a protein. Kuettner points to this material inhibiting endothelial cell proliferation which could retard neovascularization and subsequent healing of bone.

The wound healing glycoside compositions in U.S. Pat. No. 4,456,596 issued June 26, 1984 to Schäfer show effect only on punch and burn wounds in guinea pigs and only effects the final phase of wound healing relating to proliferation of epithelial cells after vascularization and capillarization. Calder in U.S. Pat. No. 2,935,448 issued May 3, 1960 uses phosphatide by-products derived from corn oil production to treat osteoarthritis.

BRIEF DESCRIPTION OF THE DRAWINGS

FIG. 1 corresponds to Table I and shows increase in bone density with time.

FIG. 2 corresponds to Table II and shows results of dynamic scans.

Angiogenesis, the formation of new blood vessels, plays a critical role in a number of biological processes, both normal and pathological. It is best described as the directed ingrowth of new capillaries toward a specific stimulus, a process that involves vascular endothelial cells proliferation and chemotaxis.

Omental material is shown to have an effect in wound healing and is the subject of our co-pending application Ser. No. 805,206, filed Dec. 4, 1985.

Omental material also has effect in healing skin conditions in skin care and in cosmetics as is the subject of our co-pending application Ser. No. 811,505, filed Dec. 20, 1985. All of the above patent applications are hereby incorporated by reference.

There is no art dealing with use of omentum, omental fractions or omental lipid fractions in bone or bone wound healing. The material of the invention is thus novel as to bone healing.

Angiogenesis and chemical factors that mediate or inhibit the angiogenic process have important implications in major diseases (Auerbach, R. (1981) in Lymphokines ed E. Pick, Academic Press, Vol. 4., P. 69). Angiogenic factors have been purified from various pathological sources (Schor, A. M. et al. (1983) Tumor Angiogenesis J. Pathology 141:385) and from normal tissue in small quantities (D'Amore, P. A. et al. (1981) Proc. Nat'l. Acad. Sci. 78:3068–3072; Frederick, J. L. et al. (1984) Science 224:389–390; Burgos, H. (1983) J. Clin. Invest. 13:289–296). Normal tissue, available in large quantities, that contains potent angiogenic activity provides opportunities for isolation, structural analysis and extensive animal and clinical studies. In contrast to previously reported angiogenic factors, the lipid (±ganglioside) omentum derived factor is available quantity which makes it attractive for application and study.

Angiogenesis is an essential part of normal growth and tissue repair, and factors that mediate the angiogenic process may have important therapeutic implications in situations where an increased number of capillaries are clinically needed, such as in wound healing, organ ischemia and burns.

It is of particular interest for the orthopaedic surgeon that the omentum-derived lipid factor offers the possible hope of promoting growth of new blood vessels into areas of bone fracture, pseudarthrosis, bone graft, arthrodesis and aseptic necrosis. It is particularly relevant in displaced subcapital fractures of the femur and certain fractures of the carpal scaphoid, talus and head of the humerus which are susceptible to selective infarction of one fragment. Avascular necrosis of bone is an important contributing factor to non-union. The key to the repair of dead cortical bone is its internal invasion from viable tissue by thin-walled capillary vessels. Nevertheless, there is a limit to revascularization at least in some infarcts. The slow nature of revascularization of many bone infarcts leads to the persistence of necrotic parts for years.

There is no current data demonstrating an effect of the omental angiogenic factor on osseous vasculature.

The objectives of the present invention were:
(1) to analyze the efficacy of local administration of omental angiogenic factor on the revascularization process in autologous demineralized bone transplants.
(2) to determine the secondary impact of the omental angiogenic factor on new bone formation and bone repair.
(3) to evaluate the collagenization properties of the omental lipid factor on a bone repair model.

A chloroform-methanol extract from feline omentum has been previously reported (Goldsmith, H. et al. JAMA 252:15 P. 2034) (hereby incorporated by reference) to produce excellent angiogenic activity after a single injection into the central cornea of rabbits. This is also the subject of copending U.S. patent application Ser. No. 642,624 filed Aug. 20, 1984 hereby incorporated by reference. Ser. No. 642,624 is now U.S. Pat. No. 4,699,788 issued Oct. 13, 1987. The components of this extract have now been fractionated and the major glycosphinogolipid components characterized. The angiogenic activities, as measured by the chick chorioallantoic membrane (CAM) assay (Folkman, J. 1974) Cancer Res. 34:2109), of the fractions and purified glycosphingolipids have also been determined. Neutral glycosphingolipids and particularly gangliosides have recently been reported to be associated with a variety of cellular responses and have been shown to modulate activity of receptors of several growth factors (Bremer, E. G., et al. (1984) J. Cell. Biol. 259:6818). Our studies indicate that exogenesis glycolipids can influence the angiogenesis response in the chicken egg chorioallantoic membrane system. This information is found in copending application Ser. No. 782,724, filed Oct. 1, 1985.

Materials

HPLC grade methanol and other reagent grade solvents and chemicals were obtained from Fisher Chemical Scientific (Fairlawn, N.J.); Iatrobeads 6RS-8060 and 6RS-8010 were from Iatron Industries (Tokyo, Japan); DEAE-Sephadex (A-25) was from Pharmacia Fine Chemicals (Piscataway, N.J.); Unisil was from Clarkson Chemical Company (Williamsport, Pa.); and HPTLC plates were obtained from E. Merck (Darmstadt, Germany). Ganglioside and glycolipid standards were prepared as previously described (Velman, M. D., et al. (1977) J. Lipid. Res. 18:371–378; Ledeen, R. W., et al. (1978) in Research Methods in Neurochemistry Vol. 4 ed. Marks and R. Rodnight Plenum Publishing Corp., N.Y. P. 371–410). V. cholerae neuraminidase was obtained from Sigma Chemical Co. (St. Louis, Mo.).

Methods

Fractionation of Omentum Extracts-Omenta from adult female cats were excised and minced as previously reported (Goldsmith, et al. Supra). The omentum preparations were homogenized in cold phosphate-buffered saline (PBS) and centrifuged at 4° C. for 20 min in 250 ml plastic bottles at 1,600 g. After centrifugation, the lipid plastic bottles at 1,600 g. After centrifugation, the lipid cake was removed and homogenized in 20 volumes of chlorform-methanol (2:1). The extract was centrifuged at 200 g for 10 min to remove particulate matter and the clear supernatant was evaporated to dryness/Iin vacuo to obtain the crude lipid extract (CLE) also known as the CMFr.

The CMFr was dissolved in hexane (approximately 60 ml/10 g of extract) and 0.66 volumes of 95% ethanol added (Galanos, D. S. et al. (1962) J. Lipid. Res. 3:134). The phases were thoroughly mixed and allowed to separate. The lower phase was removed and the upper phase (hexane layer) re-extracted with 95% ethanol. The lower phases were combined and re-extracted with a fresh volume of hexane and the hexane phases combined. The phases were then taken to dryness/Iin vacuo to obtain hexane upper phase material (hexane-UP) also known as the HxCMFr and ethanol lower phase material (ethanol-LP) also known as ETCMFr. The hexane phase contained approximately 98% of the material in the CMFr and was shown to consist primarily of triglycerides as determined by Thin Layer Chromatography (TLC). Alkaline hydrolysis and GC/MS analysis of the resulting fatty acid methyl esters revealed that 14:0, 16:0, 16:1, 17:0, 18:0, 18:1 and 18:2 were the major triglyceride fatty acids.

Other hydrocarbons (e.g., pentane, cyclohexane, cyclopentane, benzene, etc.) can be used instead of hexane for the above separation. Methanol., n-propanol, and acetonitrile can be used instead of ethanol for the above separation. Other methods can also be used as seen and obvious to those skilled in the art in Kates, M. (1972) "Techniques of Lipidology: Isolation, Analysis, and Identification of Lipids", (North-Holland Elsevier P. 269–610) hereby incorporated by reference. These methods among others may include acetone precipitation, solvent partition using countercurrent distribution, column chromatography, and/or high pressure liquid chromatography.

Next a Folch partition (Folch, J., et al. (1957) J. Biol. Chem. 226:497–509) was performed. The ethanol-LP was dissolved in chloroform/methanol (2:1) (20 volumes, v/wt) and 0.2 volumes of water added and phases thoroughly mixed and allowed to separate. The upper phase was removed and the lower phase washed with 0.4 volumes of methanol/water (1:1). The upper phases were combined and both phases taken to dryness in vacuo to obtain Folch-UP and Folch-LP material.

Folch-LP material was dissolved in chloroform and subjected to chromatography on a silicic acid (Unisil) column (Vance, D. E., et al. (1967) J. Lipid. Res. 8:621). The Unisil column was eluted successively with 20 column volumes of chloroform, acetone/methanol (9:1), and methanol to obtain the neutral lipid, glycolipid and phospholipid fractions, respectively. The neutral lipid fraction consisted primarily of triglycerides and small amounts of cholesterol and free fatty acids as detected by TLC analysis. The acetone glycolipid fraction was examined by TLC and components migrating as hexosylceramide, lactosylceramide, globotriaosylceramide and globoside were present. HPLC analysis of the lower phase glycolipids showed Glc Cer (Nfa), 26%; Gal Cer (N fa), 9.6%; Glc Cer (H fa)+Gal Cer (H fa)+GaOse 2 Cer (N fa), 12%; lac Cer, 11%, GbOse Cer, 10% GbOse4Cer, 26%. The methanol phospholipid fraction was examined by TLC and components migrating as phosphatidylserine, phosphatidylcholine and sphingomyelin were present.

The Folch-UP material was dissolved in methanol/water (1:1) (approximately 20% by weight of the Ethanol-phase material) (approximately 3 ml/mg) and applied to a C18 reversed-phase cartridge (BondElut) (Williams, M. et al. (1980) J. Neurochem. 35:266–269) which was then washed with 4 volumes of methanol/water (1:1) followed by elution with 4 volumes of chloroform/methanol (2:1). The Two washes were separately collected and evaporated to dryness/fIin vacuo/fR to obtain non-lipid material (non-lipid-UP) and lipid material (lipid-UP) respectively.

The lipid-UP material was dissolved in methanol/chloroform/water (60:30:8) and applied to a DEAE-Sephadex [acetate] column (Christie, W. W. (1982) *Lipid Analysis*, Pergamon Press 2nd Ed. P. 109–110). The column was eluted with 10 volumes of the same solvent to obtain the neutral lipid upper phase fraction (neutral lipid-UP) consisting of a glycolipid migrating below globoside and small amounts of more complex glycolipids. The column was then eluted with methanol/chloroform/0.8 M sodium acetate (60:30:8) to obtain the ganglioside fraction. The fractions were evaporated to dryness/FIin vacuo/fR. The ganglioside fraction was deslated with a C18 reversed-phase cartridge as described above. HPTLC showed the presence of $GM_3$, $GM_1$, $GD_3$ and several minor polysialogangliosides (GDla and GTlb). The $GD_3$ ratio of Glc/Gal was 1:1 and the major fatty acid components were 16:01, 18:0, 18:1, 24:0 and 24:1. Neuraminadase treatment produced lactosylceramide. The liberated sialic acid was N-acetylneuraminic. A flow chart of the fractionation scheme is shown below (FIG. 1).

Omenta were extracted from feline and bovine sources as previously described Goldsmith et al. (1984) J. Amer. Med. Assn. 252:15, pp. 2034–2036 to yield a chloroform methanol extract (CME) also known as the CMFr. This CMFr is further extracted with hexane to yield a neutral lipid fraction from the CMFr known as the HxCMFr. Other lipid extraction methods can be used as well. The invention is not limited by the extraction method described above which is for illustrative purposes. Other extraction methods such as affinity or high pressure or antibody column chromatography can be used as well with or without a $N_2$ atmosphere for example to prevent oxidation. Bovine, ovine and porcine omenta as well as other mammalian omenta can also be extracted in the like manner. Other organic solvents can be used as well as supercritical gas extraction as with $CO_2$ (application filed Oct. 31, 1985 Ser. No. 793,622 now U.S. Pat. No. 4,749,522 hereby incorporated by reference) and cryogenic methods such as omental subdivision in liquid $N_2$ with subsequent use of the above or other extraction techniques the subject of application Ser. No. 811,507, filed Dec. 20, 1985, now abandoned, continued as Ser. No. 148,127 filed Jan. 26, 1988 issued as U.S. Pat. No. 4,776,173.

In supercritical gas extraction $CO_2$ can be used at a temperature of 38°–39° C. and a pressure of 3500 psiq. An amount of $CO_2$ 200 times the sample weight can be used for example in achieving a purified sample.

Insoluble polar material such as gangliosides remains as a residue while non-polar materials such as triglycerides are found in the extracts. Other gases such as nitrogen, hydrogen, oxygen, ozone, fluorine, or organic gases can be used as well. Thus these conditions avoid extraction with toxic materials or inefficient extraction or use of expensive and time-consuming extractions and materials.

It is also possible to use detergents to isolate lipids from omentum. Lipids are displaced from homogenized cell membranes, or other complexes involving proteins, by amphipathic detergent molecules which render the proteins "soluble" in aqueous media. The released lipid material is recovered by flotation after centrifugation.

A list of possible detergents is given in Tables A and B below. These are used in concentrations ranging from 0.1 to 2.0% (w/v) and a pH from 7.0 to 8.0.

TABLE A

DETERGENTS WITH FLEXIBLE HYDROPHOBIC REGIONS

| Detergent type | Structural formula | Formal (and trivial) name |
|---|---|---|
| Strongly ionic | (alkyl chain)–O–S(=O)(=O)–$O^-Na^+$ | Sodium dodecylsulphate |
| | (alkyl chain)–$N^+$($CH_3$)$_3$ $Br^-$ | Cetyltrimethylammonium bromide |
| "Weakly" ionic | (alkyl chain)–N($CH_3$)(C(=O)–)–$CH_2$–$COO^-Na^+$ | Sodium dodecyl-N-sarcosinate (sarkosyl) |

TABLE A-continued
DETERGENTS WITH FLEXIBLE HYDROPHOBIC REGIONS

| Detergent type | Structural formula | Formal (and trivial) name |
|---|---|---|
| Zwitterionic | 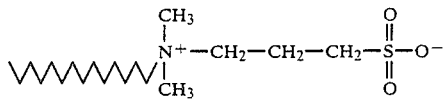 | Sulfobetaine (Zwittergent)[a] Palmitoyllysolecithin |
| "Weakly" Zwitterionic | 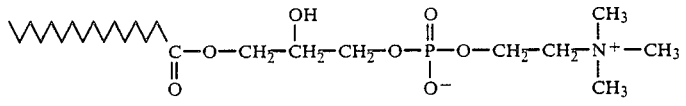 | Dimethylalkylamine oxides (Ammonyx LO)[b] |
| Non-ionic | 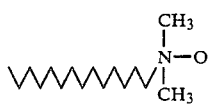 | Polyoxyethylene alcohol (Brij series, Lubrol W. AL. P series) Polyoxyethylene nonylphenol (Triton N series Igepal CO series Surtonic N series Emulgen series |
| Non-ionic with branched hydrophobic region | 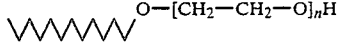 | Polyoxyethylene proctyl phenol (Triton X series Igepal CA series Nonide: P40) |

[a] Available from Calbiochem-Behring, Serva.
[b] Available from Onyx Chemical Co., 190 Warren Street, Jersey City NJ 07032 U.S.A.

TABLE B
DETERGENTS WITH RIGID HYDROPHOBIC REGIONS

| Detergent type | Structural formula | Formal (and trivial) name |
|---|---|---|
| Strongly ionic | 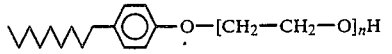 | Sodium cholate |
| "Weakly" ionic | 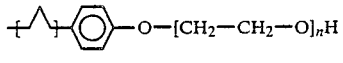 | Sodium taurocholate |
| Zwitterionic | 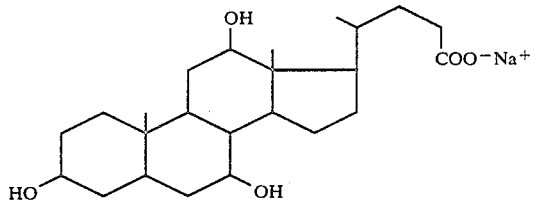 | CHAPS[a] |

TABLE B-continued
DETERGENTS WITH RIGID HYDROPHOBIC REGIONS

| Detergent type | Structural formula | Formal (and trivial) name |
| --- | --- | --- |
| Non-ionic | 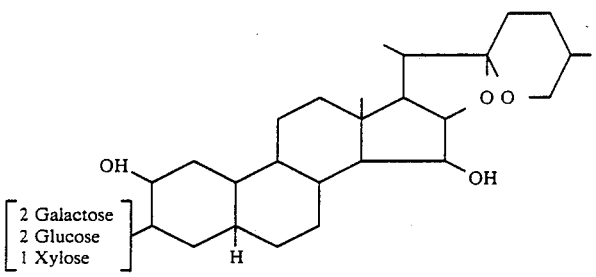 | Digitonin |

[a]3-[(3-cholamidopropyl)dimethylammonio]-1-propanesulphonate, available from Calbiochem-Behring, Serva.

To test the effects of omental materials and compositions on bone healing, a rat model was developed. Using Sprague-Dawley inbred male rats (375-420 g) a 5 mm segmental defect was created in the midshaft of the right femur and the bone marrow removed. The femur was then internally fixed by means of a polyethylene plate with four K-wires screws. The defect was replaced with a 5 mm segmental demineralized bone isograft (from inbred rats). The material to be tested, as for example the CMFr, was delivered through a mini-osmotic pump (model 2ML2 - Alza Corp. Palo Alto) inplanted into a subcutaneous pocket made in the scapular region of the animal. The pump tubing was tunnelled down to the paw and adfixed through the polyethylene plate into the center of the tubular implant. The pump provided continous, round-the-clock controlled delivery of bioactive agents. The pump's delivery rate of vehicle was 5 microl/h and was predetermined at manufacture. It is constant for 14 days at 37° C. The pump's capacity was 2 ml. The animals were divided into three groups of 50 each:

Group A: omental lipid angiogenic factor—feline CMFr
Group B: omental lipid control—feline HxCMFr
Group C: saline control (Ringer's solution) Animals were sacrificed at , 1,2,3,6,9,12 weeks and studied radiographically, histologically and biomechanically tested for bone formation and union. Quantitative and qualitative assessment of peripheral perfusion and bone graft vascularization were performed by means of dynamic radioisotopic bone-imaging and microangiography.

MATERIAL AND METHODS

Demineralized bone transplants.

Demineralized bone matrix was chosen as the transplant material for three reasons: potential of demineralized 1. the osteogenic potential of demineralized bone matrix is now firmly established since the work of Urist who showed that demineralized compact bone has the ability to act as an osteoinductive and osteoconductive material stimulating bone formation and bridging large bone defects (Science 150:893 (1965), Clin. Orthop. 59:59 (1968), Proc. Nat'l. Acad. Sci. USA 81: (1984), Science 220:680 (1983), J.B.J.S. 34A:443 (1952)).

2. the remineralization process that takes place in the demineralized bone matrix can be easily visualized radiographically and evaluated to provide an estimation of new bone formation.

3. previous studies, using demineralized bone matrix in similar experimental modes, are available for comparative purposes (Wittbjer, et al. J. Plast. Reconstr. Surg. 17:109 (1983), Wilson, P. D., et al., J.B.J.S. 47A:1629 (1965).

Preparation of demineralized bone matrix segments.

Demineralized bone segments were prepared from femurs and tibias of inbred male Sprague-Dawley rats (375-420 g). The bones were mechanically cleaned, cut on both ends and the bone marrow was removed by saline wash. The bone segments were immediately transferred into 0.6 N hydrochloric acid solution and demineralized for seventy-two hours at 4 degrees Celsius by continuous stirring with three acid changes. The acid was then removed by washing the bones with distilled water for eight hours at 4 degrees Celsius. The bone segments were then defatted and stored in small plastic tubes in 70% alcohol at −70 degrees Celsius until use (8-42 days). The ash weight of these bone segments accounted for 1.6% of the dry weight after ashing at 600 degrees Celsius for 24 hours.

Osmotic pump

To provide easy and adequate local administration of the material, a totally implantable drug pump was chosen as the delivery system. The mini-osmotic pump (Alzet* osmotic pump, Alza Corporation, Palo Alto, Calif.) consists of a collapsible reservoir of flexible impermeable material surrounded by a sealed layer containing an osmotic agent, all of which is contained by a semi-permeable membrane. When the pump is put into an aqueous environment, it imbibes water at a rate that is controlled by the semi-permeable membrane. The imbibed water generates hydrostatic pressure on the flexible lining of the reservoir, gradually compressing it and producing a constant flow of its content through the delivery portal. The model 2ML2 used in this experiment has been developed for delivering a specified volume of 5 microliters per hour for 14 days. These data guaranteed by the manufacturer are related to tests of pumping rate in vitro determined in isotonic saline at 37 degrees Celsius.

Specifications of model 2ML2 are:
nominal pumping rate: 5 microl./hr for 14 days at 37° C.

reservoir volume: 2.2 ml
length: 5.1 cm
diameter: 1.4 cm

At the top of the pump, a non-kinkable vinyl catheter (0.72 mm ID, intravenous tubing, Bolab, lake Havasu City, Ariz.) is attached to the flow moderator. The distal end of the catheter is connected to a 8 mm long metallic cannula (19 gauge) to provide direct local tissue microperfusion. 16 to 18 days after implantation, each spent osmotic pump is removed. The catheter is controlled to be in correct position and the pump to contain small residual volume of liquid.

Experimental design

Male Sprague-Dawley rats (375–420 g) were premedicated with 10 mg/100 g BW intra-muscular ketamine (Ketalar*). General anesthesia was induced and maintained with mask ventilation (2L 02/min, 0.8 L N20/min Fluotane mixture). 60,000 Units Procain Penicillin G was given subcutaneously. The right thigh and the scapular region were shaved and desinfected with 70% alcohol and betadine solution. Using sterile procedure the skin of the lateral thigh was incised longitudinally and so was the fascia lata. The vastus lateralis and the biceps femoris were separated and retracted on each side of the femur. The whole circumference of the midshaft of the femur was liberated from the surrounding muscles. A pre-drilled high density polyethylene plate (23×4×4 mm) was fixed to the anterior surface of the femoral shaft by four threaded Kirschner wires (diam 1.2 mm, Zimmer*). With a rotating dental saw, a 5 mm long osteoperiosteal segment was resected from the midshaft of the femur. The bone marrow was removed from the proximal and distal bone segments by intramedullary lavage with isotonic saline. Demineralized bone transplants, pre-soaked in warm Ringer's solution for one hour prior to implantation, were then prepared. In order to provide a mechanically strong, non-collapsible implant, a small diameter segment, usually from the tibia, was inserted into the femoral segment transplant. This double-coated demineralized bone graft was cut to size to fill the defect, placed in the defect, and stabilized by two cerclages (Stainless steel). A subcutaneous pocket, designed to receive the pump, was then prepared in the interscapular region of the animal by blunt dissection with a hemostat. Immediately prior to implantation, the pump was filled under aseptic conditions with the material to be tested pre-warmed at 37° C. The pump with its catheter was then implanted. The tubing was tunnelled down to the paw, underneath the fascia of the quadriceps, and connected to the cannula pre-inserted through the center of the polyethylene plate, just over the transplanted bone matrix. A generous amount of slack was left to the tubing. The muscles and the skin were then closed over the plate. The animals were placed in collective cages (2 animals/cage) and fed on a standard laboratory rat food.

The animals were divided into three groups of 50 each according to the material subjected to local infusion:

Group A: CMFr = chloroform-methanol extracted fraction of the omentum, containing the angiogenesis activity.
Group B: HxCMFr = hexane phase material from the 95% ethanol hexane partition of CMFr (=lipid control)
Group C: Ringers Solution (=saline control)

The animals are sacrified at 1, 2, 3, 6, 9 and 12 weeks, studied radiographically, histologically and biomechanically tested for bone formation and union. Quantitative and qualitative assessment of peripheral perfusion and bone graft vascularization are performed by means of dynamic radioisotopic bone-imaging and microangiography.

Radiographic Phodensitometry

The light intensity measured on the radiograph of bone through a photodensitometer is a reflection of degrees of radiodensity which can be attributed to the mineral content of bone.

Under general anesthesia AP radiographs of both femurs were performed. X-rays were then analyzed through a digital densitometer, giving the optical density of each region as a measurement of the bone density. Four points, 1 mm diam., were measured in each graft area, and one point in the surrounding soft tissues. To eliminate individual variability, both femurs were analyzed and the results expressed as a ratio of the right femur to the left.

Estimation of new bone formation:

per cent new bone = $R/L \times 100$ where
$R = STr - [(n1 + n2 + n3 + n4)/4]$, on the right side, and
$L = STl - [(m1 + m2 + m3 + m4)/4]$ on the left side.

The animals were radiographed under general anesthesia at 2, 4, 6 and 9 weeks after surgery. With the animal lying prone, skeletal radiographs of both femurs were performed using constant exposure conditions (tube voltage 42 KV, current 10 ma.) and source-target distance (90 cm). The remineralization process in the demineralized bone matrix transplant was evaluated through a digital densitometer (Nuclear Associates Inc. Model II 07-424). The optical density in the graft area was measured in four pre-selected points of 1 mm diameter (proximal, distal, superior cortex, inferior cortex). One measurement was taken in the surrounding soft tissues to correct for the soft tissue density component. The average optical density of the graft was then subtracted from the optical density of the soft tissues and the resulting value is called Index$_{OD}$. The same procedure was repeated on the analogous anatomical area of the contra-lateral femur. All the exposure requirements being constant for each animal, the only variable parameter was the film emulsion response. To correct for this variation, a transformation equation, proposed by Burstein et al (J. Biomech. 4:155 (1971)), is used which converts density readings to relative densities on a scale from 1 to 10. Consequently, a film dark value and light value, together with the Index$_{OD}$ value are fit into the following transformation equation:

$$T(\text{Index}, D, L) = \frac{10}{9(C - L)/(D - L) + 1}$$

where
$D$ = film dark value
$L$ = film light value

To normalize individual animal variability, the results were expressed as a ratio of the right femur (osteotomy side) to the left (unoperated) femur and reflect the amount of new bone formation as a percentage of the contralateral unoperated side.

Thus: % new bone formation = $R/L \times 100$

Dynamic radioisotopic bone-imaging

Prior studies (R. W. Nutton et al. Mayo Clinic J.B.J.S. 67A:763–770 (1985) J. Orthop. Res. 2:67–74

(1984)) have demonstrated that the angiographic phase of a bone scan reflects bone blood flow, and dynamic imaging during this phase may have value in quantifying the vascularity of osseous lesions. This method is based on previous studies that demonstrated that for a period of time after intravenous injection of a radioactive indicator, the integral of the counts per unit of time (count rate) of gamma irradiation emitted by the indicator from a specific organ is directly proportional to the fraction of cardiac output to that organ (Anderson, C., Manual for the Examination of Bone, Boca. Raton, Fla.: CRC Press, 1982 P.71, Beggren, A., et al., J.B.J.S. 64A:799(1982)). The area under the one-minute uptake curve of Tc-99m HDP appears to be linearly related to blood flow and is not affected by diffusion limitation, which affects diphosphonates at high blood flow rate.

The animal was anesthetized with halothane and positioned supine on the scanning table with the hind legs rotated externally so that the medial aspect of each femur was in contact with the collimator of the gamma camera connected to a on-line computer. The position of the legs was secured with adhesive tape; care was taken to avoid restricting the blood flow to the limbs. A low-energy, all-purpose collimator is used, and the gamma camera (General Electric 500 AC) is interfaced with a on-line computer (Star, Data General, General Electric) for storage of data on a magnetic disk (IBM Diskette 2D).

Using a 25 gauge butterfly infusion needle, the left cardiac ventricle was punctured through the fourth intercostal space. At time zero, a bolus injection of 500 microCu Sodium Pertechnetate ($99m_{To}NaD_4$-specific activity 14 KeV, Syncore Pharmaceuticals, Garden City, N.Y.) was injected and the computer records serial 2-second images for 60 seconds. Similar regions of interest, 25 pixels in area ($64 \times 64$ matrix), were selected on the computer screen. Regions of interest were placed over the areas of the grafts and included as well some of the surrounding soft tissues. Corresponding region of interest about analogous anatomical area were drawn on the left femur. Using the computer, counts per second were plotted against time in seconds to produce time-activity curves for each region of interest during the initial sixty seconds of the flow study. Each curve was integrated and the mean counts per second calculated by:

$$\text{mean counts/sec.}^{-1} = \frac{1}{(t_{60} - t_1)} \int_{t_i}^{t_{60}} R(t)\, dt$$

where R(t) is the count rate, $t_i$ is the time at the first detection of radioactivity, and $t_{60}$ is the time at the end of the dynamic flow study. Results were expressed as ratio of the right to the left leg and were directly proportional to the ratio of blood flow to those regions being evaluated. The blood flow to the soft tissues overlying the bone graft area contributed to the total radioactivity that was detected over the bone. This method was based on previous studies that demonstrated that for a period of time after intravenous injection of a radioactive indicator, the integral of the counts per unit of time (count rate) of gamma irradiation emitted by the indicator from a specific organ is directly proportional to the fraction of cardiac output to that organ. The examples below are meant to be illustrative of the invention and not to limit it. Thus porcine, bovine, ovine and feline as well as other mammalian omental materials can be used as extracted above or by any other known extraction methods in the art.

EXAMPLE I

The bone density in the three groups of rats, measured by digital densitometry, are shown in table I and in FIG. 1. There is a significant increase, compared with the two control groups, in the bone density in the graft area at two ($p<0.001$) and four ($p<0.0001$) six ($p<0.001$) and nine ($p<0.01$) weeks (unpaired student t test). Although not statistically significant, however group B shows a slight overall increase in bone density compared to group C. Thus it can be seen that the CMFr enhances earlier mineralization of bone within 2 weeks.

FIG. 1 represents the bone density measured in the bone transplant as a percentage of the contralateral side at different time-intervals. The greatest increase in bone density occurred in the first two weeks post-surgery. Once local delivery of the angiogenic material had stopped and the pump removed from the animal, group A behaved like the control groups, but because the quantity of mineral deposition in the graft was higher in the early phase, the difference was still significant at 12 weeks.

EXAMPLE II

The results of the dynamic scans of all the regions of interest are shown in table II and in FIG. 2.

There was a significant increase, compared with the two control groups, in the activity detected over the bone graft area during the first minute after injection in group A (angiogenic factor). This increase is statistically significant at one (p 0.001), two (p 0.001) and three (p 0.01) weeks (unpaired Student t test) and is a maximum at two weeks post-surgery. The difference decreases then rapidly to become not significant at six weeks. Although there is no statistically significant difference between group B (lipid control) and group C (saline control) at all-time intervals, however group B shows a slight overall increase in activity compared to group C.

FIG. 2 represents the one-minute uptake of Pertechnetate as a percentage of the contralateral unoperated side at different time-intervals. The high peaks at one week post-surgery reflect increased vascularization in the bone and in the surrounding soft tissues, secondary to the trauma of surgery. At two weeks, when local delivery of angiogenic substance has stopped, the uptake decreases more rapidly in group A to approximate the control groups at 12 weeks.

TABLE I

| RADIOGRAPHIC PHOTODENSITOMETRY | | | | |
|---|---|---|---|---|
| | BONE DENSITY (% OD) | | | |
| | 2 WEEKS | 4 WEEKS | 6 WEEKS | 9 WEEKS |
| GROUP A | 45 ($\pm 2.72$) | 58 ($\pm 3.62$) | 68 ($\pm 3.42$) | 84 ($\pm 5.92$) |
| | n = 32 | n = 16 | n = 10 | n = 15 |
| p* (A/B) | <0.001 | <0.001 | <0.02 | NS |
| GROUP B | 28 ($\pm 1.50$) | 42 ($\pm 2.59$) | 55 ($\pm 4.37$) | 75 ($\pm 5.01$) |
| | n = 23 | n = 24 | n = 10 | n = 15 |
| p* (B/C) | NS | NS | NS | NS |
| GROUP C | 25 ($\pm 1.92$) | 39 ($\pm 2.61$) | 49 ($\pm 2.59$) | 64 ($\pm 3.63$) |
| | n = 17 | n = 27 | nm = 10 | n = 18 |
| p* (A/C) | <0.001 | <0.001 | <0.001 | <0.01 |

Results are shown as mean and standard error of the mean
NS = not significant
*unpaired Student T test

TABLE II

| | RADIOISOTOPIC BONE-IMAGING ($^{99m}TcNaO_4$-) | | | | |
|---|---|---|---|---|---|
| | DYNAMIC SCANS (% Counts/Sec.) | | | | |
| | 1 WEEK | 2 WEEKS | 3 WEEKS | 6 WEEKS | 12 WEEKS |
| GROUP A | 1.62 (±0.04) n = 9 | 1.55 (±0.06) n = 8 | 1.34 (±0.04) n = 7 | 1.28 (±0.05) n = 6 | 1.09 (±0.06) n = 3 |
| p° (A/B) | <0.01 | <0.002 | NS | NS | NS |
| GROUP B | 1.42 (±0.05) n = 7 | 1.28 (±0.03) n = 8 | Δ | 1.22 (±0.07) n = 5 | 1.05 (±0.08) n = 3 |
| p° (B/C) | NS | NS | | NS | NS |
| GROUP C | 1.35 (±0.03) n = 6 | 1.23 (±0.08) n = 8 | 1.18 (±0.02) n = 6 | 1.17 (±0.08) n = 5 | 1.04 (±0.09) n = 3 |
| p° (A/C) | <0.001 | <0.001 | <0.01 | NS | NS |

Results are shown as mean and standard error of the mean
Δ data lost in computer files
NS = not significant
°unpaired Student T test

EXAMPLE III

Microangiography

The injection was done under anesthesia in order to avoid postmortem changes (intravascular clotting, agonal vasospasm . . . ) with death at the conclusion of the procedure.

For microangiography under inhalation anesthesia (e.g. fluorothane), a laparotomy was performed through a midline incision. The abdominal aorta and the vena cava were dissected and exposed. After systemic heparinization, both vessels were ligated proximally and selective cannulation of the abdominal aorta was then carried out using a 25 gauge polyethylene catheter. The vena cava was vented to prevent overfilling. Ringer's lactate solution, warmed at 37° C. and to which a vasodilator (lidocaine 0.5%, 0.5 ml) has been added, was then infused through the arterial catheter until all blood was displaced and clear return obtained from the vena cava. When exsanguination was completed, as determined by the character of the outflow, the isotonic solution was replaced by the contrast medium made up of a 50% suspension of barium sulfate (Micropaque, Picker Corporation, Cleveland, Ohio 44143) in Ringer's lactage, mixed with Blue Evans. Thirty ml of contrast material was slowly injected manually at a constant pressure to avoid rupture of small vessels. Micropaque is mixed with 5% gelatin (to reduce extravasation at the time of infusion, and to prevent leakage when the specimen is cut.

Prior to injection, the mixture was constantly stirred and warmed in a water bath at 37° C. Delivering of the contrast medium was made at a constant pressure of 150 mm Hg through a mechanical injector or through the laboratory air supply by a pressure - release mechanism. A considerable excess of contrast material was injected at a pressure slightly higher than physiologica to insure filling of all the vessels. Care must be taken not to overfill the vessels in order to avoid dilatation or rupture. The length of time of injection was 30 minutes.

Satisfactory injection was confirmed by rapid blueing of both legs. When the injection procedure was completed, the abdominal vessels were ligated distally. The animal was then killed by anesthetic overdose and left in a refrigerator overnight at 4° C. The following day, the perfused leg was disarticulated at the hip joint and a radiography (Faxitron, 65 Kv, 4 min.) was performed to confirm adequate injection of the vasculature of the leg. Unsuccessfully or poorly injected specimens were discarded. The leg was then placed in 10% neutral buffered formalin solution for two days. The femur was removed, cleaned of soft tissues and further fixed for three or five days in 10% buffered formalin solution at low temperature. When fixation was obtained, the bone was subsequently decalcified in 5% nitric acid for 48 hours, dehydrated in increasing alcohol concentrations and embedded in paraffin after removal of the plate. Longitudinal sections 500 microns or 2 mm thick were cut from the central portion of the specimen including the entire dimineralized bone implant as well as both junction areas between the host bone and the graft on a freezing microtonic and contact microangiographs were made using Kodak SO-403 high resolution film in a Faxitron unit and processed with Kodak D-19 Developer. Slices of paraffin-embedded tissue were mounted between two layer of clear plastic wrap (Saran) to prevent curling and drying and placed in direct contact with the photographic emulsion using the Faxitron.

Magnifications of the microradiographs up to 10× were accomplished and the microvasculature in the bone implant was qualitatively and quantitatively evaluated in terms of formation and distribution of blood vessels as well as speed of the angiogenic response.

The vascular supply, as revealed by microangiograms, could then be correlated with the cellular and matrical response, as revealed by histological preparation.

Microangiograms revealing the vascular supply were correlated with the cellular and material response shown by the histological preparations.

Vascularization leads to formation of new blood vessels (angiogenesis) and also to increased blood flow. This increased blood flow can be quantitatively assessed by the 1-minute uptake Tc-99m dynamic bone.

Qualitative assessment of the angiogenic effect was done by static Tc-99m bone scan, microangiography and histology.

Dynamic Tc-99m HDP bone scan tested out whether or not angiogenesis in the bone implant is associated with concomitant blood flow increase.

Microangiograms were examined for blood vessel formation, distribution of blood vessels, speed of the angiogenic response and pattern characteristics of demineralized bone matrix implant vascularization.

EXAMPLE IV

Histology

After satisfactory microangiograms of each 500 microns slice is obtained, selected slices were fused to a block of fresh paraffin and sectioned further on a sliding histological microtome.

Two animals in each group are studied histologically at 1, 2, 3, 6, 9 and 12 weeks. The bones are fixed in 10% buffered formalin for 6 to 8 days and decalcified in 5% nitric acid for 48 to 72 hours. The bones are cut in a strictly longitudinal manner and then embedded in paraffin. Sections 5 microns thick are stained with hematoxylin and eosin, as well as safranin O and PAS, and evaluated under light microscopy for bone and cartilage formation, cortical union and vascular ingrowth.

In addition, selected slices obtained from each microangiogram, are fused to a block of fresh paraffin and further sectioned and stain with PAS. This procedure permits histological study of the identical slice of tissue from which the microangiogram is made. In this way, the exact relationship between injected capillaries and cellular elements in the same tissue slice can be evaluated.

Sections either 5 or 10 micrometers thick were made and mounted on standard glass slides. Routinely they were stained with hematoxylin and eosin as well as safranin O and PAS. Some are stained with Weigert's elastic tissue stain for identification of arteries. Injected vessels were readily identifiable by the yellow granules of Micropaque in their lumina. This procedure permited histological study of the identical slice of tissue from which the microangiogram is made. In this way, the exact relationship between injected capillaries and cellular elements in the same tissue slice was evaluated.

EXAMPLE V

At 2,4,6,8 and 12 weeks, 15 animals have had AP radiographs of their femur graded for bone formation, bridging, union and remodelling.

At 12 weeks, 15 animals were sacrificed and torque tested for osseous union according to the method of Burstein (ref) - ultimate strength, energy absorption, displacement and load/displacement slope (Burstein, A. H. and Frankel, V. H.: J. Biomech. 4:155 (1971). The site of failure was noted and graded according to the method of White J.B.J.S. 59A:188 (1977).

For biomechanical testing, the femurs were freed of their soft tissues and evaluated for union by gentle manipulation. Mechanically unstable bones were not tested with torsional loading. If stable, the polyethylene plate still attached to the right femur was partially incised (90%) in its mid-portion three times in order to decrease the torsional resistance of the plate without compromising the strength of the underlying bone. Great care was taken so as to prevent any contact with or nicking of the cortical bone. Right and left femurs were then potted in epoxy resine and tested to failure in torsion in a standardized torsion apparatus. Torque and angular displacement were recorded on an oscilloscope and then photographed. The stiffness of the bone was calculated by drawing a tangential line to the load deformation curve after torque loading at one unit. Energy absorption was calculated by determining the surface area under the torque-angular deformation curve from the onset of load to the failure point. Torque at failure displacement corresponding to the maximal torque, stiffness and energy absorption was expressed as a percentage of the corresponding values of the contralateral femur.

A modified White's fracture classification grading system (Table III) was used to evaluate the failure behavior of the tested bones, White, Supra. Type I fracture of this classification is defined as a non-union of the implanted bone graft to the host bone. Type II fracture is defined as a fracture through the implanted bone graft in a mechanically stable bone. A type III fracture occurs through both the implanted bone and the host bone. A type IV fracture, is a fracture through the host bone alone.

7 animals at 1 and 2 weeks, 5 at 3 week, and 3 at 4,6,9 and 12 weeks have had quantitative and qualitative assessment of bone graft vascularization by means of dynamic radioisotope bone imaging and microangiography, and were fixed histologically and examined in a longitudal manner for osseous bone formation and vascular invasion—graded and scaled. As seen in Table III the experimental group (A) bore twice the maximum torque of the saline control group(C) showing greater strength in the bones of the treated animals.

Thus the composition of the invention can be used in a number of bone healing process namely healing of breaks and fractures of all types, enhancement of healing in cases of delayed union. This can be useful in healing fractures in horses as well. The angiogenic composition can also be useful for soft tissue disease, in healing tendons and ligaments. It would also be useful to enhance the take in bone grafts.

TABLE III

| | BIOMECHANICS: FRACTURE DISTRIBUTION (WHITE'S CLASSIFICATION) | | | |
|---|---|---|---|---|
| | I | II | III | IV |
| Group/Type | (Non-Union) | (UNION) | | |
| A (n = 20) | 5(25%) | 5(25%) | 6(30%) | 4(20%) |
| B (n = 20) | 9(45%) | 2(10%) | 9(45%) | 0(0%) |
| C (n = 20) | 12(80%) | 4(20%) | 3(15%) | 1(5%) |
| Strength (maximal torque) | | | | |
| Group A | R = 26.40 NM | | R/L = 0.42 | |
| | L = 63.04 NM | | | |
| Group C | R = 11.68 NM | | R/L = 0.22 | |
| | L = 52.32 NM | | | |

Union/Non-Union A/C: $X^2 = 5.01$ (d/ = 1/ = D $p$ 0.01)

What is claimed is:

1. Method for enhancement of bone healing in mammals which comprises treating damaged mammalian bone with pharmaceutically and physiologically active amounts of isolated omental lipid consisting essentially of ganglioside to enhance healing of the damage wherein the damage comprises a fracture, osteoarthritis, arthrodesis, osteonecrosis or a bone graft and wherein treating the damaged bone with the omental ganglioside-containing lipid enhances at least one of bone density, bone perfusion or bone strength.

* * * * *